United States Patent
Lemer

(10) Patent No.: US 7,112,811 B2
(45) Date of Patent: Sep. 26, 2006

(54) SCREEN FOR PROTECTION AGAINST IONISING RADIATION EMISSIONS

(75) Inventor: Pierre-Marie Lemer, Nantes (FR)

(73) Assignee: Lemer Protection Anti-X Par Abreviation Societe Lemer Pax, Carquefou (FR)

(*) Notice: Subject to any disclaimer, the term of this patent is extended or adjusted under 35 U.S.C. 154(b) by 0 days.

(21) Appl. No.: 10/511,581

(22) PCT Filed: Apr. 17, 2003

(86) PCT No.: PCT/FR03/01247

§ 371 (c)(1),
(2), (4) Date: Oct. 18, 2004

(87) PCT Pub. No.: WO03/088267

PCT Pub. Date: Oct. 23, 2003

(65) Prior Publication Data

US 2005/0173658 A1    Aug. 11, 2005

(30) Foreign Application Priority Data

Apr. 17, 2002  (FR) .................................. 02 04768

(51) Int. Cl.
*G21F 1/00*    (2006.01)

(52) U.S. Cl. ................. 250/515.1; 250/519.1; 250/517.1; 250/455.11; 378/203

(58) Field of Classification Search ............ None
See application file for complete search history.

(56) References Cited

U.S. PATENT DOCUMENTS

| 3,308,297 | A | * | 3/1967 | Mansker ............... 250/515.1 |
| 4,581,538 | A | | 4/1986 | Lenhart |
| 4,965,456 | A | * | 10/1990 | Huettenrauch et al. .. 250/515.1 |
| 5,220,175 | A | * | 6/1993 | Cole .................. 250/515.1 |
| 6,278,125 | B1 | | 8/2001 | Belek |

FOREIGN PATENT DOCUMENTS

| EP | 0 345 548 | 12/1989 |
| WO | WO 01 84558 | 11/2001 |

* cited by examiner

*Primary Examiner*—Jack Berman
*Assistant Examiner*—Zia R. Hashmi
(74) *Attorney, Agent, or Firm*—Young & Thompson

(57) ABSTRACT

A protective screen includes a front wall (1), connected to a lateral wall (2) running perpendicular or essentially perpendicular to the front wall (1), the walls (1, 2) including transparent panels (8, 10) over at least a part of the height thereof. The upper part (8) of the front wall (1) is inclined forwards, forming an overhang which permits the operator to approach the working region and with two holes (11, 12) to permit the passage of the operator's arms.

13 Claims, 2 Drawing Sheets

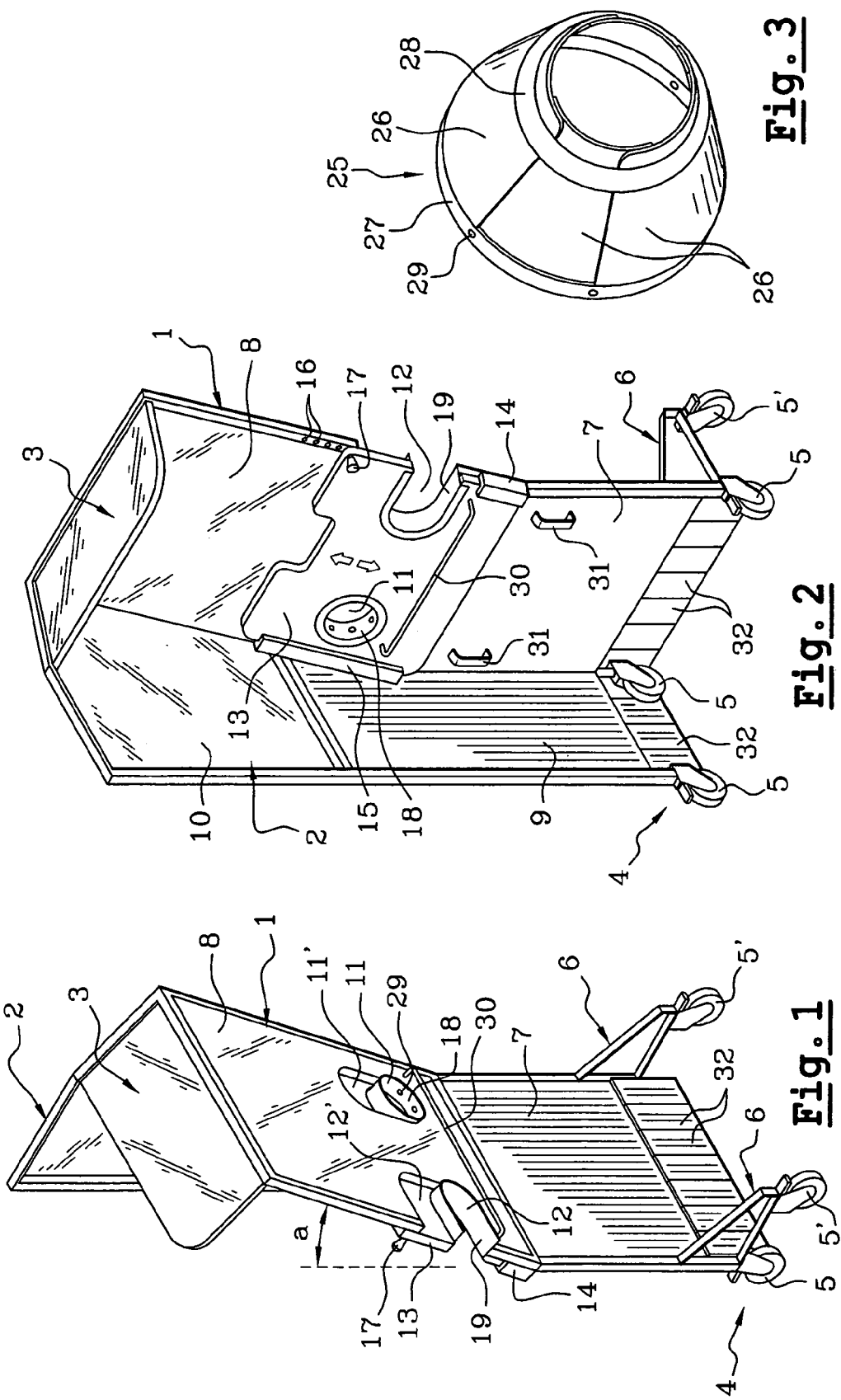

SCREEN FOR PROTECTION AGAINST IONISING RADIATION EMISSIONS

BACKGROUND OF THE INVENTION

The present invention relates to a radioprotective screen, and more particularly a screen used in medicine or other to protect an operator against ionising radiation emissions, for instance the X or gamma rays.

For certain interventions on patients, such as catheterism type, placement of pacemaker, vascular, neurological or urological tests . . . the operator (technician, doctor, surgeon or other) must be protected against the ionising radiations to which the patient is exposed.

The existing protection structures consist of clothing such as vests, jackets or aprons made of radioprotective material.

There exist also screens made of panels or assemblies of panels of appropriate material placed vertically and directly on the ground or by dint of a supporting skid.

But the clothes of radioprotective material do not ensure optimal protection for the operator, since in particular they do not cover the whole body (head, legs, arms and feet), and also since weight loads to which these clothes are exposed. On the other hand, the current radioprotective screens, for example as described in the documents U.S. Pat. No. 3,308,297 or EP-A-0 345 548, are not adapted to enable an operator to work comfortably and in complete safety.

SUMMARY OF THE INVENTION

The present invention provides a new structure of radioprotective screen which is particularly efficient and interesting for the operator on an ergonomic plane.

The object of the invention provides on the one hand better visibility for the operator, and on the other hand greater comfort when being placed behind the screen, within the framework of his intervention. This operator thus benefits from better working conditions, without wearing heavy clothes, which enables him to intervene with greater accuracy and higher efficiency, and thus in complete safety.

The radioprotective screen according to the present invention consists of a front wall, associated with a side wall which extends at right angle or substantially at right angle from one of the sides of said front wall, and both these walls include transparent panels over a portion at least of the height thereof. The upper section of the front wall is tilted forward, thereby overhanging, for enabling the operator to come closer to the intervention zone, and it is fitted with two orifices for letting through said operator's arms.

Still according to the invention, the front wall of the screen is formed of a lower panel vertical or substantially vertical, prolonged by an upper panel whereof a portion at least is made of transparent material, which upper panel is tilted forward, forming an angle ranging between 10 and 30° with respect to the vertical. Preferably, the corresponding angle ranges between 15 and 20° with respect to the vertical.

According to a particular embodiment, the front wall is formed of a lower panel of opaque material which extends over a height ranging between 60 and 100 cm, prolonged by an upper panel which extends up to a level corresponding at least to the operator's height, i.e. of the order of 2 m.

According to another particularity, one at least of the orifices for letting through the operator's arms is provided with an oversleeve of radioprotective material intended to grip the operator's wrist or forearm for better protection. This oversleeve is advantageously in the form of an <<iris>>, composed of flexible strips mounted on a circular crown. This crown may be associated with the rim of said orifice by any appropriate means, such a push-button for instance; and the strips, four in number for instance, made of leaded rubber-type material, overlap and are preferably maintained by a flexible wristband which is situated outside, close to the external mouthpiece of the oversleeve.

Still according to the invention, one of the orifices for letting through the arms is situated close to the angle formed by the front and lateral walls, and the other orifice is situated on the free edge of said front wall, at the same level as the latter and open laterally to facilitate the movement of the corresponding arm.

According to a first possible embodiment, the upper front panel fitted with orifices for letting through the arms includes a lining system composed of a mobile panel. This mobile panel is fitted itself with orifices for letting through the arms, matching the orifices of the front wall; these latter orifices, oblong in shape and oversized with respect to the orifices of said mobile panel, extend over the whole surface scanned by said orifices of said lining panel. This particularity enables to adjust the height of the orifices for letting through the operator's arms.

Preferably, the mobile lining panel is guided on the front wall by means of rails arranged laterally. This mobile panel is on the other hand lockable on the front wall, according to several positions adapted to the height of the operator, by means of an anchoring finger co-operating with an index arranged on the structure of said front wall.

According to another possible embodiment, and still to enable adjustment in height of the orifices for letting through the arms, the front wall and the side wall form an assembly mounted to slide vertically on a frame or substructure fitted with castor wheels.

The screen then includes advantageously a system for controlling the assembly composed of the front wall and the lateral wall, in the form of actuator(s) driven by a control member such as a pedal or a push-button for instance.

Still according to the invention, the lower section of the screen is in the form of a frame or substructure fitted with castor wheels mounted at the different ridges with, moreover, at least one additional castor wheel mounted to protrude on the front face of the front wall, carried by a console, enabling to increase the sustentation perimeter of said screen, and thereby its stability.

According to another arrangement of the invention, the screen includes, attached to the front and lateral walls, or to the chassis or substructure, flexible strips of radioprotective material, such as leaded rubbed for instance, enabling notably to let through pedals, cables or other accessories connected to the material necessary to certain types of medical interventions or others.

According to still another arrangement, the screen includes, on the external and internal faces of the front wall, small bars or profiles enabling the installation of sterile fields, arranged below the level of the orifices for letting through the arms.

According to still another arrangement of the invention, an additional wall of radioprotective material acting as a ceiling, extends at least partially between the front wall and the side wall of the screen.

According to still other particularities, the screen according to the invention includes a flexible curtain for protecting the operator's back, as well as a removable resting arm for supporting said operator.

BRIEF DESCRIPTION OF THE DRAWINGS

But the invention will be further illustrated, without being limited thereto, by the following description of two particular embodiments, given solely for exemplification purposes and represented on the drawings wherein:

FIG. 1 represents, in perspective and as a front three-quarter view, a first possible embodiment of a radioprotective screen according to the present invention;

FIG. 2 represents the screen of FIG. 1, still in perspective, showing its inner portion;

FIG. 3 represents, at enlarged scale, a protective oversleeve in the form of iris, adaptable at the circular orifice for letting through an arm, and in particular the left arm of the operator in the example of screen represented on FIGS. 1 and 2;

DESCRIPTION OF THE PREFERRED EMBODIMENTS

Figure 6:
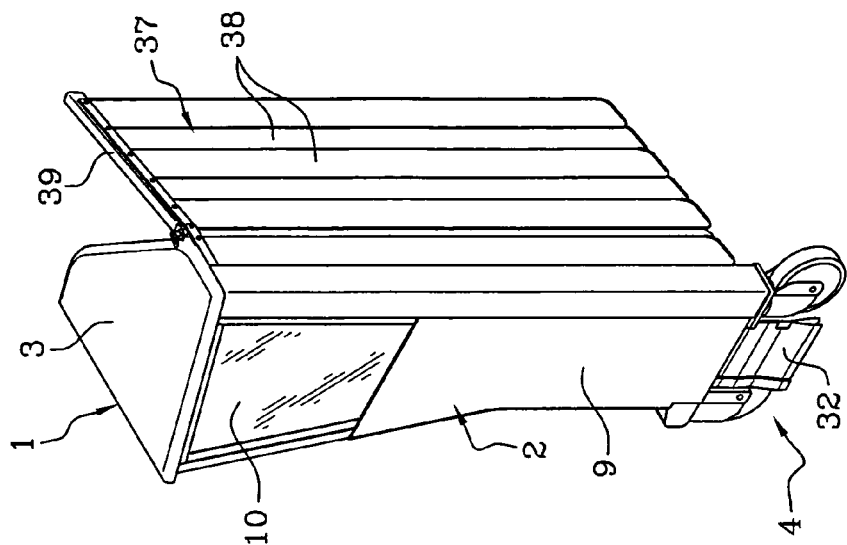
FIG. 6 is a perspective, rear three-quarter view, of the screen illustrated on FIGS. 4 and 5.

As represented on FIGS. 1 and 2, the radioprotective screen comprises a front wall 1 and, arranged at right angle or substantially at right angle, a side wall 2.

The upper section of the screen includes an additional wall acting as a ceiling 3, which may extend on the space, in all or in part, situated between the upper rims of the front 1 and lateral 2 walls.

This type of screen, intended to protect an operator against ionising radiation emissions, is composed of panels of appropriate radioprotective material. The different panels are supported by a metal skeleton, for instance of aluminium, which integrates a shield enabling continuous radioprotection at all the junctions.

This screen comprises lower panels which are opaque (for instance made of wooden panels shielded with lead sheets), and upper panels which are transparent (for instance of leaded glass or leaded Plexiglas) to provide front and lateral visibility to the operator which intervenes notably in medicine, for operations where the patient is exposed to radiations.

The substructure 4 of the screen is fitted with castor wheels 5 which enable easy displacement thereof. It should be noted that the castor wheels 5 are arranged at each ridge of the lateral and front walls; on the other hand, additional castor wheels 5' are arranged before the front wall 1, supported by consoles 6 integral therewith, in order to increase the surface of the sustentation perimeter of the screen, and hence the stability thereof. The different castor wheels 5, 5' are preferably pivoting and fitted with a releasable unlocking brake.

The front wall 1 comprises a lower section 7 composed of a vertical opaque panel, and of an upper section 8 composed of a transparent panel.

This transparent panel 8 is tilted forward, i.e. towards the operating field. Its tilt, of an angle a ranging between 10 and 30° with respect to the vertical, and preferably ranging between 15 and 20°, enables the operator to lean forward during intervention, and thus to come closer to the operating zone, for greater visibility and greater comfort, notably.

The side wall 2 extends vertically sideways; it also includes a lower opaque panel 9 and an upper transparent panel 10 which provides lateral visibility to the operator, in particular for monitoring his patient. This side wall 2 matches the dihedral shape of the front wall 1; the transparent panel 10 has substantially trapezoid shape.

The ceiling wall 3 is here made of transparent material, but it might similarly be made of opaque material if greater visibility is irrelevant.

The dimensions of the different walls are selected to enable reception of all operators' heights. Thus, the front wall 1 and the side wall 2 may be of the order of 2 m in height, for instance.

The lower panel 7 of the front wall 1 extends up to a point which corresponds for instance to the operating table; this lower panel may extend over a height ranging between 60 and 100 cm, preferably close to 80 cm.

The upper transparent panel 8 of the front wall 1 extends therefore between the level of the operating table, i.e. environ 80 cm, and a height of the order of 2 m. It includes in its lower section, i.e. above the operating table, orifices 11 and 12 for letting through the operator's arms, to enable the latter to intervene on a patient, and thus practically and reliably.

Particular means are provided on this radioprotective screen to enable to move vertically the orifices 11 and 12 for letting the arms through, to order possibly to adapt their level according to the height of the operator.

Thus, these orifices 11 and 12 are arranged, on the one hand in the panel 8 of the front wall 1, and on the other hand in a lining panel 13 arranged inside the screen. This internal lining panel 13 is arranged on the internal face of the upper panel 8 of the front wall 1; it is provided mobile parallel to said panel 8, guided into lateral rails 14 and 15 integral with the front wall 1, and its position is established by means of an index 16 co-operating with an anchoring finger 17. The indexing finger 16 is composed of several orifices spaced vertically on the lateral rim of the panel 8; the anchoring finger 17 is integral with the mobile panel 13 and it is arranged to engage into one of the orifices of the index 16, relative to the level of positioning requested of the orifices 11 and 12 for letting through the arms.

The orifices 11 and 12 arranged in the mobile panel 13 are advantageously fitted with rings 18, 19, which can be disassembled and treated in an autoclave readily, fastened by means of captive screws.

The panel 8 of the front wall 1 includes orifices 11' and 12' oblong in shape, oversized with respect to the orifices 11 and 12 of the mobile panel 13, and whereof the sizes, shapes and positions are adapted to the travel of said lining panel 13. These orifices 11' and 12' remain masked permanently by the lining panel 13, regardless of the positioning thereof.

The lining panel 13 is for instance made of the same radioprotective material as the upper panel 8 of the front wall 1.

The orifice 11 situated in the mobile panel 13 is a circular orifice; it is situated close to the angle formed by the front 1 and lateral 2 walls. This circular orifice 11 is adapted for letting through the operator's left arm, for the embodiment represented on FIGS. 1 and 2.

The orifice 12 provided in the mobile panel 13 is arranged towards the free rim of the front wall 1, and it is open laterally, actually in the form of a horizontal U to enable the operator to remove his arm easily and to keep great freedom of movement.

For increased protection of the operator, the passage of the ionising radiations through the orifice 11 should be limited by fitting said orifice with a protection oversleeve 25 in the form of an <<iris>>. This iris 25 is represented individually on FIG. 3. It is composed of an assembly of strips 26, here four in number, which overlap partially and which are attached to a circular crown 27 whereof the diameter correspond substantially to the diameter of the orifice 11.

These strips 26 are for instance made of leaded rubber-type material; they are preferably retained elastically at their mouthpiece, by means of a wristband 28.

The oversleeve 25 in the form of iris is fixed in the orifice 11, on the ring 18, by dint of its circular crown 27, by means of a system of push-buttons 29 for instance.

On FIGS. 1 and 2, it can be noted that the screen according to the invention is fitted with small bars or profiles 30, on the one hand on the lining panel 13, and on the other hand on the external face of the panel 8, intended notably for the attachment of sterile fields. On the internal face of the panel 7, the presence of two handling grips 31 should also be noted.

At its lower section, i.e. between the frame or substructure 4 on which the castor wheels 5, 5' are fixed and the ground, the screen includes a flexible protection apron composed of a juxtaposition of strips 32. These strips 32 may superimpose each other partially; they are made of leaded rubbed, for instance, and they let through accessories such as control cables or pedals useful for certain types of intervention.

These strips 32 are attached by any appropriate means to the lower section of the panels 7 and 9 of the walls 1 and 2 respectively.

Figure 5:
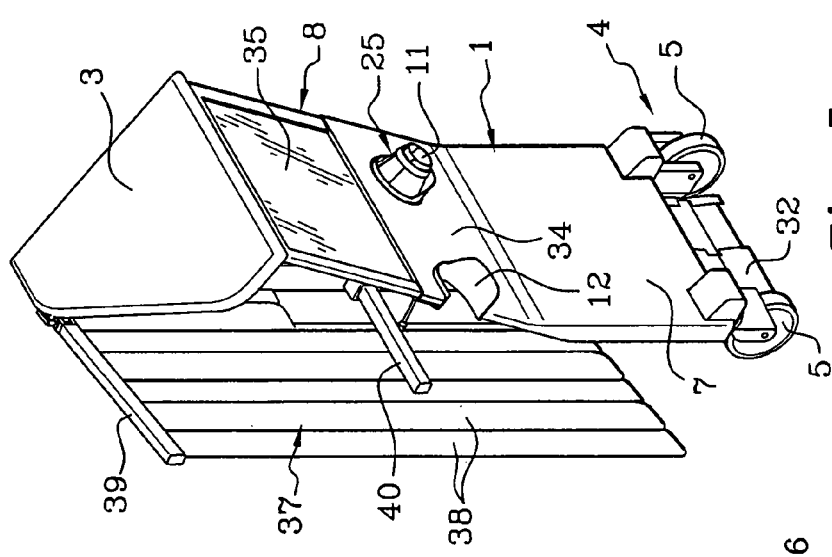
FIG. 5 shows the screen of FIG. 4, in perspective and as a rear three-quarter view.
Figure 4:
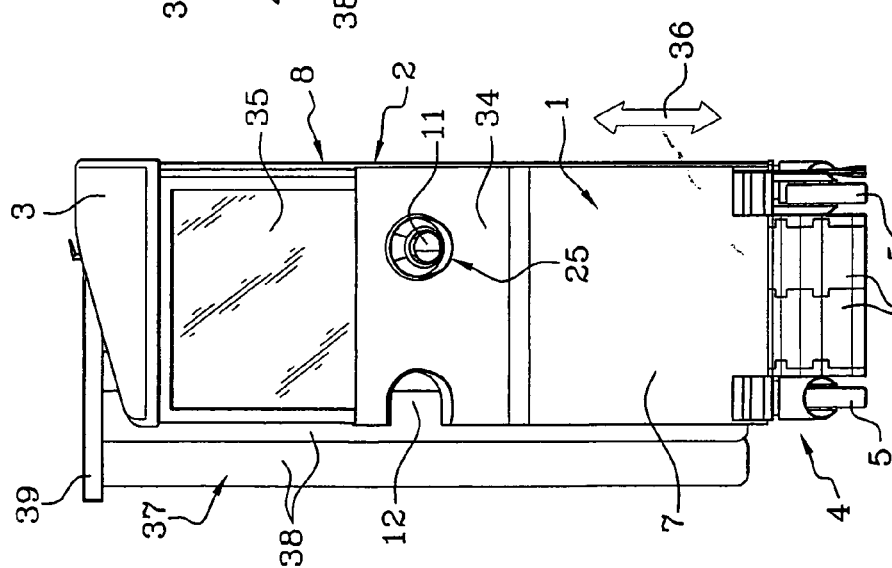
FIG. 4 is a front view of a second possible embodiment of a radioprotective screen according to the invention.

FIGS. 4 to 6 show an embodiment variation of a radio-protective screen according to the invention.

In this embodiment variation, the sections common to the previous embodiment keep the same reference signs for easier understanding thereof.

The front wall 1, the side wall 2 and the ceiling wall 3 supported by a frame or substructure 4 fitted with castor wheels 5 can be seen.

The front wall 1 comprises a lower section 7 composed of a vertical opaque panel, and a upper section 8 tilted forward by an angle ranging between 10 and 30° (and preferably between 15 and 20°) with respect to the vertical. This upper section 8 comprises an opaque zone 34 situated in the alignment of the lower panel 7, fitted with two orifices 11 and 12 for letting through the operator's arms; this opaque zone 34 is topped with a transparent zone 35.

The orifice 11 is circular and it is associated with a protection oversleeve 25 protruding outwardly; the orifice 12 is in the form of a horizontal U, open laterally. As for the embodiment described previously, the orifices 11 and 12 are advantageously fitted with dismountable rings.

The side wall 2 extends vertically and it includes a lower opaque section 9 topped with an upper transparent section 10. In this embodiment, the ceiling wall 3 is opaque.

The front 1 and lateral 2 walls as well as the ceiling 3 are supported by a metal skeleton of shielded aluminium.

This metal skeleton may be adjustable in height with respect to the supporting substructure 4, in order possibly to adapt the level of the orifices 11 and 12 according to the operator's height. This possibility of adjustment, illustrated by the double arrow 36 of FIG. 4, is obtained by a sliding assembly of the metal skeleton in question on the substructure 4. This sliding assembly may for instance be realised by means of guiding slides integral with the substructure, engaging into the vertical stanchions of the metal skeleton; one or several actuators, of hydraulic type or others, form the control system of the movement, driven by a control member such as pedal, push-button, joystick or other.

The corresponding adjustment system does not show on the figures.

As can be seen on FIGS. 4 to 6, the screen according to the invention includes a flexible curtain 37 enabling the protection of the operator's back. This flexible curtain 37 is advantageously composed of a juxtaposition of flexible strips 38 of leaded rubber, mounted on a supporting arm 39 fixed cantilever to the upper section of the screen, for instance on the free rim of the ceiling wall 3, or on the upper rim of the side wall 2.

Preferably, the supporting arm 39 is mounted articulated around a vertical axis to enable placement and retraction of the curtain, or simply for adjusting its position behind the operator.

This flexible curtain 37 forms a kind of mobile wall for efficient and complete radioprotection.

FIG. 5 also shows the presence of an arm 40 which extends horizontally, cantilever from the side wall 2, substantially halfway up the screen, intended to serve as a resting member for the operator's back or kidneys.

This resting and supporting arm 40 is preferably removable; it may be mounted articulated on the side wall 2, associated with a retractable cross-bracing rod.

FIGS. 4 to 6 also show the presence of the strips 32 of leaded rubber, supplementing the protection at the lower section, in the alignment of the front 1 and lateral 2 walls. These protection strips 32 may be attached to the substructure 4 and/or on the lower rim des front 1 and lateral 2 walls.

The different accessories described, such as profile 30, curtain 37 or resting arm 40 may form optional equipment and be arranged individually or in combination on either of both embodiments described, or on neighbouring versions.

The open orifice 12 may possibly include a kind of protection oversleeve, similar to the oversleeve 25 but open laterally. On the other hand, the screen may include two circular orifices for letting the arms through; in such a case, both these orifices will be advantageously fitted with protection oversleeves 25.

The invention claimed is:

1. A screen made of radioprotective material for ensuring protection of an operator against X ray-type ionising radiation emissions or the like, comprising:
    a front wall having a lower vertical section and an upper transparent section that is tilted forward at a fixed angle of 10° to 30° relative to said lower vertical section over an operator work zone, said upper transparent section having two orifices therein for an operator's arms; and
    a vertical side wall extending away from the operator work zone generally at a right angle from one side of said front wall, said side wall having one side conforming in shape to said fixed angle between said lower vertical section and said upper transparent section, and said side wall having a transparent panel over a portion of a height of said side wall.

2. The screen of claim 1, wherein said fixed angle is from 15° to 20°.

3. The screen of claim 1, wherein said lower vertical section is 60 to 100 cm in height and said upper transparent section extends to a height of about 2 m.

4. The screen of claim 1, wherein one of said two orifices has an oversleeve of radioprotective material, said oversleeve comprising flexible strips mounted on a circular crown that is associated with a rim of said one of said two orifices, said flexible strips overlapping and being maintained by a flexible wristband near an external mouthpiece of said oversleeve.

5. The screen of claim 1, wherein one of said two orifices is adjacent to said side wall and another of said two orifices is at an opposite free edge of said front wall and has a U-shape open to said free edge.

6. The screen of claim 1, further comprising a movable panel on a side of said upper transparent section opposite the operator work zone, said movable panel having further orifices that correspond in location to said two orifices, said two orifices being oblong in shape so that said two further orifices open to the operator work zone when said movable panel is moved relative to said upper transparent section.

7. The screen of claim 6, wherein one of said two orifices is adjacent to said side wall and another of said two orifices is at an opposite free edge of said front wall and has a U-shape open to said free edge, and wherein said one of said further orifices that corresponds to the U-shaped one of said two orifices is also U-shaped and open to said free edge.

8. The screen of claim 6, wherein one of said further orifices has an oversleeve of radioprotective material, said oversleeve comprising flexible strips mounted on a circular crown that is associated with a rim of said one of said further orifices, said flexible strips overlapping and being maintained by a flexible wristband near an external mouthpiece of said oversleeve.

9. The screen of claim 6, further comprising a lock for adjusting a position of said mobile panel, said lock including plural indices on said front wall and an anchoring finger associated with said mobile panel that engages one of said plural indices.

10. The screen of claim 1, further comprising flexible strips of leaded rubber-type material that depend from a bottom of said lower vertical section.

11. The screen of claim 1, further comprising a ceiling that is attached to tops of said side wall and said upper transparent section.

12. The screen of claim 1, further comprising a flexible curtain that extends from a rear part of said side wall generally parallel to said front wall to a distance at least corresponding to an extent of said front wall.

13. The screen of claim 1, further comprising a frame of adjustable height that has wheels, said front and side walls being carried by said frame.

* * * * *